United States Patent
Gonzalez-Toro et al.

(10) Patent No.: US 10,357,668 B2
(45) Date of Patent: Jul. 23, 2019

(54) INHIBITING COLOR FADING WITH LAYER-BY-LAYER FILMS

(71) Applicant: L'OREAL, Paris (FR)

(72) Inventors: Daniella Gonzalez-Toro, Union, NJ (US); Jim Singer, South Orange, NJ (US)

(73) Assignee: L'OREAL, Paris (FR)

(*) Notice: Subject to any disclaimer, the term of this patent is extended or adjusted under 35 U.S.C. 154(b) by 412 days.

(21) Appl. No.: 15/087,703

(22) Filed: Mar. 31, 2016

(65) Prior Publication Data

US 2017/0281515 A1 Oct. 5, 2017

(51) Int. Cl.
- *A61Q 5/00* (2006.01)
- *A61Q 5/02* (2006.01)
- *A61K 8/81* (2006.01)
- *A61K 8/898* (2006.01)

(52) U.S. Cl.
CPC .......... *A61Q 5/004* (2013.01); *A61K 8/8129* (2013.01); *A61K 8/8147* (2013.01); *A61K 8/8152* (2013.01); *A61K 8/8188* (2013.01); *A61K 8/898* (2013.01); *A61Q 5/02* (2013.01); *A61K 2800/5424* (2013.01); *A61K 2800/5426* (2013.01); *A61K 2800/594* (2013.01); *A61K 2800/88* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 4,824,664 A | 4/1989 | Tarral et al. | |
| 6,383,472 B1 | 5/2002 | Dupuis et al. | |
| 7,398,824 B1 | 7/2008 | Wang et al. | |
| 7,744,655 B2 | 6/2010 | De Boni et al. | |
| 8,277,790 B2 | 10/2012 | Verboom et al. | |
| 8,523,953 B2 | 9/2013 | Hoffmann | |
| 8,993,068 B2 | 3/2015 | Koberstein et al. | |
| 9,074,034 B2 | 7/2015 | Kharlampieva et al. | |
| 9,186,314 B2 | 11/2015 | Nguyen et al. | |
| 2009/0071494 A1 | 3/2009 | Nguyen et al. | |
| 2010/0008885 A1* | 1/2010 | Daly | A61K 8/463 424/70.27 |
| 2011/0142892 A1 | 6/2011 | Daly | |
| 2013/0209388 A1 | 8/2013 | Erazo-Majewicz et al. | |
| 2013/0272979 A1* | 10/2013 | Nguyen | A61K 8/585 424/60 |
| 2015/0125879 A1 | 5/2015 | Li et al. | |
| 2015/0157545 A1 | 6/2015 | Rizk | |
| 2016/0120284 A1* | 5/2016 | Crne | A61Q 5/065 132/208 |

FOREIGN PATENT DOCUMENTS

| | | |
|---|---|---|
| EP | 1321131 A2 | 6/2003 |
| WO | WO-99/55295 A1 | 11/1999 |

OTHER PUBLICATIONS

Buck M.E., et al. "Functionalization of Fibers Using Azlactone-Containing Polymers: Layer-by-Layer Fabrication of Reactive Thin Films on the Surfaces of Hair and Cellulose-Based Materials," ACS Applied Materials & Interfaces, vol. 2, No. 5, 2010, pp. 1421-1429.

Michel, M. et al., "Deposition Mechanisms in Layer-by-Layer or Step-by-Step Deposition Methods: From Elastic and Impermeable Films to Soft Membranes with Ion Exchange Properties," ISRN Materials Science, vol. 2012, Article ID 701695, pp. 1-14.

International Search Report dated Jul. 7, 2017 for corresponding application PCT/US17/24019.

* cited by examiner

*Primary Examiner* — Jyothsna A Venkat

(74) *Attorney, Agent, or Firm* — Polsinelli PC

(57) ABSTRACT

The present disclosure relates to methods for inhibiting color fading in hair and for improving the color durability and stability of artificial color of hair. The methods entail forming a layer-by-layer (LbL) film on hair, and optionally forming a cationic surface layer on the LbL film. The LbL film is formed by applying a cationic silane layer on the hair and subsequently applying an anionic polymer layer on the cationic silane. Multiple cationic silane layers and anionic polymer layers can sequentially be added as desired. Finally, the LbL film may comprise a cationic surface layer.

10 Claims, No Drawings

INHIBITING COLOR FADING WITH LAYER-BY-LAYER FILMS

FIELD OF THE DISCLOSURE

The present disclosure relates to methods for inhibiting color fading in artificially colored hair, which thereby improves the color durability and stability of hair color. The methods entail forming layer-by-layer (LbL) film on hair.

BACKGROUND

There are many products available for changing the natural color of hair. The process of changing the color of hair can involve either depositing an artificial color onto the hair, which provides a different shade or color to the hair, or lifting the color of the hair, such as for example, from a dark brown shade to a medium brown or a light brown shade. Hair color can be changed using permanent, semi-permanent, or temporary hair coloring products.

Many consumers desire a permanent color change and therefore use products containing permanent dyes. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Newly, permanently colored hair usually has a vibrant, shiny, and rich appearance. Unfortunately, however, in just a few short weeks, or in some cases even less, the color begins to fade. For instance, gorgeous rich brown colors become muddy and dull, beautiful shades of blonde turn brassy, and vibrant reds do not look so vibrant anymore. As described herein, the inventors of the instant disclosure have developed methods and kits that improve color durability by preventing color fading from hair.

SUMMARY OF THE DISCLOSURE

The present disclosure relates to methods for improving the color durability and stability of hair color by inhibiting color fading. Color fading is inhibited by applying a layer-by-layer (LbL) film on the hair, which optionally includes a surface layer. LbL is a method for creating thin films through serial assembly of individual layers that rely on complementary interactions to associate with one another. Typically, the LbL films are applied to artificially colored hair by: (a) applying a cationic silane layer on the hair; and subsequently; (b) applying an anionic polymer layer on the cationic silane layer; and (c) optionally, repeating (a) and (b) to form additional layers. In some cases, cationic surface layer (d) is applied to the outermost layer of the LbL film.

The cationic silane layer, the anionic polymer layer, and the cationic surface layer are typically separately and sequentially applied to the hair in solutions, such as aqueous solutions, comprising the cationic silanes and anionic polymers.

An exemplary but non-limiting method comprises: (a) applying a solution comprising 0.1 wt. % to 25 wt. % of a cationic silane to the hair and forming a cationic silane layer on the hair; subsequently, (b) applying a solution comprising 0.1 wt. % to 5 wt. % of a polystyrene to the cationic silane layer and forming an anionic polymer layer on the cationic silane layer; and (c) optionally, repeating (a) and (b) to form one or more additional layers; thereby forming a layer-by-layer (LbL) film on the artificially colored hair. Additionally, a solution comprising 0.1 wt % to 20 wt. % of a polyacrylamide having quaternary ammonium groups may finally be applied to the outermost layer of the LbL film to form a cationic polymer surface layer. Often, a drying step is employed after each of the cationic or anionic polymer solutions is applied to the hair. For instance, after applying the solution of cationic silane or anionic polymer (or the cationic outer layer), the treated hair is then dried to remove substantially all of the liquid in the solution leaving behind a cationic silane layer and/or the anionic polymer layer on the hair.

The instant disclosure also relates to kits comprising the components for treating hair with LbL films. For example, professional hair practitioners or individual consumers can use the kits to treat hair and inhibit color fading. The kits typically include: (a) a cationic silane, or a solution comprising the cationic silane, for forming a cationic silane layer on the hair; and separately, (b) an anionic polymer, or a solution comprising the anionic polymer, for forming an anionic polymer layer on the cationic silane layer. Finally, the kit may optionally include (c) a separate cationic polymer, or cationic polymer solution, for forming a cationic polymer surface layer on the LbL film.

DETAILED DESCRIPTION OF THE DISCLOSURE

The instant disclosure relates to methods for applying LbL film layers on hair, methods for inhibiting color fading in artificially colored hair, and kits comprising the components necessary to create LbL films on hair and inhibit color fading. More specifically, LBL films may be formed on hair with a method comprising:

(a) applying a cationic silane layer on the hair; and subsequently (b) applying an anionic polymer layer on the cationic silane layer; and (c) optionally, repeating (a) and (b) to form additional layers; thereby forming a layer-by-layer (LbL) film on the artificially colored hair. Further, a cationic surface layer (d) may be applied to the outer surface of the LbL film. The cationic surface layer may comprise the cationic silane of (a), or it may comprise a different cationic polymer (or a combination of the same and different cationic polymers).

The cationic silane layer of (a), in some cases, is an aminoalkoxysilane layer, for example, a compound of the following formula:

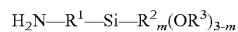

wherein $R^1$ is $C_1$-$C_6$-alkylene, $C_5$-$C_6$-cycloalkylene or $C_5$-$C_6$-arylene, each of which may be optionally substituted by one or two $C_1$-$C_3$-alkyl groups, and $R^2$ and $R^3$, independently of one another, are $C_1$-$C_6$-alkyl or $C_5$-$C_6$ cycloalkyl, each of which may optionally be substituted by one or two $C_1$-$C_3$-alkyl groups, and m is 0, 1 or 2.

In some instances, the aminoalkoxysilane may be selected from the group consisting of 3-aminopropyltrimethoxysilane, N-(2-aminoethyl)-3-aminopropyltrimethoxysilane, (3-triethoxysilylpropyl)-diethylenetriamine, 3-aminopropyltriethoxysilane (APTES), N-(2-aminoethyl)-3-amino-propyltriethoxysilane, (3-triethoxysilylpropyl)-diethylentriamine, 3-aminoethyltriethoxysilane (AETES), 3-aminopropylmethyldiethoxysilane (APMDES), and N-cyclohexylaminomethyltriethoxysilane. Likewise, in some cases, the aminoalkoxysilane is aminoalkoxysilane is 3-aminopropyltriethyoxysilane (APTES).

The anionic polymer layer of (b) may include, for example, an anionic polymer selected from the group consisting of polyacrylic acid, polymethacrylic acid, carboxyvinylpolymer, an acrylate copolymer, a sulfonate polymer, a carboxymethycellulose a carboxy guar gum, a copolymer of ethylene and maleic acid, an acrylate silicone polymer, and a mixture thereof. In some cases, the anionic polymer may be a sulfonate polymer such as polysulfonic acid, polystyrene sulphonate, a copolymer of methacrylic acid and acrylamidomethylpropane sulfonic acid, a copolymer of acrylic acid and acrylamidomethylpropane sulfonic acid, and a mixture thereof.

The cationic surface layer of (d), when present, may include, for example, a cationic polymer selected from the group consisting of a polyacrylamide having quaternary ammonium groups, polyquaternium, a quaternized protein or protein hydrolysate, a silicone-based cationic polymer, a quaternized or non-quaternized vinylpyrrolidone/dialkylaminoalkyl acrylate or methacrylate copolymer, a cellulose ether derivative containing quaternary ammonium groups, a cationic cellulose derivative, a cationic polysaccharide, a polymer consisting of piperazinyl units and of divalent alkylene or hydroxyalkylene radicals, a water-soluble polyaminoamide prepared by polycondensation of an acidic compound with a polyamine, a polyaminoamide derivative resulting from the condensation of polyalkylenepolyamines with polycarboxylic acids followed by an alkylation with difunctional agents, a polymer obtained by reaction of a polyalkylenepolyamine containing two primary amine groups and at least one secondary amine group with a dicarboxylic acid, a methyldiallylamine or dimethyl-diallylammonium cyclopolymer, a quaternary diammonium polymer, a polyquaternary ammonium polymer, a homopolymer or copolymer derived from acrylic or methacrylic acid containing ester or amide units substituted with a group containing an amine or quaternary ammonium function, a quaternary vinylpyrrolidone or vinylimidazole polymer, a polyamine, a methacryloyloxyethyltrimethylammonium chloride crosslinked polymer, and a mixture thereof. In some instances, the cationic polymer may be a polyacrylamide having quaternary ammonium groups, such as polyacrylamidopropyltrimonium chloride (INCI), also described as a homopolymer of acrylamido-N-propyltrimethylammonium chloride.

The LBL films are typically formed on hair by sequentially applying separate solutions comprising the cationic silanes and anionic polymers. For instance, the LbL films are typically formed by:

(a) applying a solution comprising a cationic silane to the hair and forming a cationic silane layer; followed by (b) applying a separate solution comprising an anionic polymer to the cationic silane layer and forming an anionic polymer layer; and (c) optionally, repeating (a) and (b) to form additional layers.

Additionally, the surface of the LbL film may include a cationic surface layer formed by:

(d) applying a solution comprising a cationic polymer to the LbL film and forming a cationic surface layer.

The solutions of cationic silanes and anionic polymers are cosmetically acceptable carriers, which may be aqueous solutions (or solutions of other cosmetically acceptable carriers, which may or may not include water). The cosmetically acceptable carrier may also or alternatively comprise a hydrophilic organic solvent and/or an amphiphilic organic solvent, wherein the hydrophilic organic solvent is a monohydric $C_1$-$C_8$ alcohol, a polyol such as propylene glycol, ethylene glycol, butylene glycol, hexylene glycol and glycerol, a polyethylene glycol having from 6 to 80 ethylene oxides, a mono or di-alkyl isosorbide; and the amphiphilic organic solvent is a a polypropylene glycol (PPG) or a propylene glycol alkyl ester or alkyl ether of PPG.

The solutions of the cationic silanes of (a) may include, 0.01 wt. % to 50 wt. %, 0.01 wt. % to 40 wt. %, 0.01 wt. % to 30 wt. %, 0.01 wt. % to 20 wt. %, 0.01 wt. % to 10 wt. %, 0.01 wt. % to 5 wt. %, 0.05 wt. % to 50 wt. %, 0.05 wt. % to 40 wt. %, 0.05 wt. % to 30 wt. %, 0.05 wt. % to 25 wt. %, 0.05 wt. % to 20 wt. %, 0.05 wt. % to 15 wt. %, 0.1 wt. % to 50 wt. %, 0.1 wt. % to 40 wt. %, 0.1 wt. % to 30 wt. %, 0.1 wt. % to 25 wt. %, 0.1 wt. % to 20 wt. %, 0.1 wt. % to 15 wt. %, 0.5 wt. % to 50 wt. %, 0.5 wt. % to 40 wt. %, 0.5 wt. % to 30 wt. %, 0.5 wt. % to 25 wt. %, 0.5 wt. % to 20 wt. %, 0.5 wt. % to 15 wt. %, 0.5 wt. % to 20 wt. %, 1 wt. % to 20 wt. %, 2 wt. % to 20 wt. %, 3 wt. % to 20 wt. %, 4 wt. % to 20 wt. %, 5 wt. % to 20 wt. %, 7 wt. % to 20 wt. %, 10 wt. % to 15 wt. %, of cationic silane, based on the total weight of the solution comprising the cationic silane.

Similarly, the solutions of anionic polymer of (b), may include, 0.01 wt. % to 50 wt. %, 0.01 wt. % to 40 wt. %, 0.01 wt. % to 30 wt. %, 0.01 wt. % to 20 wt. %, 0.01 wt. % to 10 wt. %, 0.01 wt. % to 5 wt. %, 0.05 wt. % to 50 wt. %, 0.05 wt. % to 40 wt. %, 0.05 wt. % to 30 wt. %, 0.05 wt. % to 20 wt. %, 0.05 wt. % to 10 wt. %, 0.05 wt. % to 5 wt. %, 0.1 wt. % to 50 wt. %, 0.1 wt. % to 40 wt. %, 0.1 wt. % to 30 wt. %, 0.1 wt. % to 20 wt. %, 0.1 wt. % to 10 wt. %, 0.1 wt. % to 5 wt. %, 0.5 wt. % to 50 wt. %, 0.5 wt. % to 40 wt. %, 0.5 wt. % to 30 wt. %, 0.5 wt. % to 20 wt. %, 0.5 wt. % to 10 wt. %, 0.5 wt. % to 5 wt. %, or 0.1 wt. % to 3 wt. % of anionic polymer, based on the total weight of the solution comprising the anionic polymer.

Finally, the solutions of cationic polymer of (d), may include, 0.01 wt. % to 50 wt. %, 0.01 wt. % to 40 wt. %, 0.01 wt. % to 30 wt. %, 0.01 wt. % to 20 wt. %, 0.01 wt. % to 10 wt. %, 0.01 wt. % to 5 wt. %, 0.05 wt. % to 50 wt. %, 0.05 wt. % to 40 wt. %, 0.05 wt. % to 30 wt. %, 0.05 wt. % to 25 wt. %, 0.05 wt. % to 20 wt. %, 0.05 wt. % to 15 wt. %, 0.1 wt. % to 50 wt. %, 0.1 wt. % to 40 wt. %, 0.1 wt. % to 30 wt. %, 0.1 wt. % to 25 wt. %, 0.1 wt. % to 20 wt. %, 0.1 wt. % to 15 wt. %, 0.5 wt. % to 50 wt. %, 0.5 wt. % to 40 wt. %, 0.5 wt. % to 30 wt. %, 0.5 wt. % to 25 wt. %, 0.5 wt. % to 20 wt. %, 0.5 wt. % to 15 wt. %, or 0.5 wt. % to 20 wt. % of cationic polymer, based on the total weight of the solution comprising the cationic polymer.

In some instances, the weight ratio of the cationic silanes of (a) to the anionic polymer of (b) in the LbL is from 25:1 to 1:1, from 25:1 to 5:1, from 20:1 to 5:1, or from 18:1 to 8:1. In some instance, the ratio of the anionic polymer of (b) to cationic polymer of (d) in the LbL is from 1:0.1 to 1:25, from 1:0.1 to 1:20, from 1:0.5 to 1:20, from 1:0.5 to 1:15, or from 1:1 to 1:15.

In some instances, the methods according to the instant disclosure, such as a method for inhibiting color fading in artificially colored hair, may comprise the following procedure:

(a) applying an aqueous solution comprising 0.1 wt. % to 25 wt. % of a cationic silane to the hair and forming a cationic silane layer on the hair, which may or may not include drying the solution comprising the cationic silane that has been applied to the hair; and subsequently (b) applying a solution comprising 0.1 wt. % to 5 wt. % of a polystyrene to the cationic silane layer and forming an anionic polymer layer on the cationic silane layer, which may or may not include drying the solution comprising the polystyrene (or other anionic polymer);

(c) optionally, repeating (a) and (b) to form one or more additional layers; and (d) optionally, applying a solution comprising 0.1 wt % to 20 wt. % of a polyacrylamide having quaternary ammonium groups (or other cationic polymer) to the LbL layer of (a) and (b) (or multiple layers of (a) and (b)) to form a cationic polymer surface layer, which may or may not include drying the solution comprising the polyacrylamide having quaternary ammonium groups (or other cationic polymer); thereby forming a layer-by-layer (LbL) film on the artificially colored hair.

The instant disclosure also relates to kits comprising the components for treating hair with LbL films. For example, professional hair practitioners or individual consumers can use the kits to treat hair and inhibit color fading. The kits typically include: (a) a cationic silane, or a solution comprising the cationic silane, for forming a cationic silane layer on the hair; and separately, (b) an anionic polymer, or a solution comprising the anionic polymer, for forming an anionic polymer layer on the cationic silane layer. Finally, the kit may optionally include (c) a cationic polymer, or cationic polymer solution, for forming a cationic polymer surface layer on the LbL film. The components of the kits may be limited as described above for the methods.

More exhaustive but non-limiting lists of components useful in the methods (and kits) described herein are presented below.

Cationic Silanes

Exemplary cationic silanes that may be used according to various embodiments of the disclosure include, but are not limited to, organosilanes and derivatives thereof, such as alkylsilanes, allylsilanes, and alkoxysilanes.

In some cases, the cationic silane may be chosen from alkoxysilanes comprising at least one solubilizing functional group, such as for example, methoxysilanes, triethoxysilanes, aminopropyltriethoxysilane, methyltriethoxysilane, and derivatives thereof and mixtures thereof. As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In some cases, the alkoxysilane comprising at least one solubilizing functional group may comprise two or three alkoxy functions. Likewise, in some cases, the alkoxy functional groups are chosen from methoxy and ethoxy functional groups.

According to some embodiments, the alkoxysilane comprising at least one solubilizing functional group present in the composition of the present disclosure is chosen from compounds of formula (VIII):

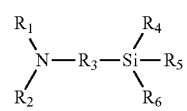

(VIII)

wherein, $R_4$ is chosen from halogen atoms, OR' groups, and $R_{11}$ groups;

$R_5$ is chosen from halogen atoms, OR" groups, and $R_{12}$ groups;

$R_6$ is chosen from halogen atoms, OR" groups, and $R_{13}$ groups;

$R_1$, $R_2$, $R_3$, R', R", R'", $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R'" may also be chosen from hydrogen;

provided that at least two groups $R_4$, $R_5$, and $R_6$ are different from $R_{11}$, $R_{12}$, and $R_{13}$, and at least two groups R', R", and R'" are not hydrogen.

The alkoxysilane comprising at least one solubilizing functional group may also be chosen from compounds of formula (IX):

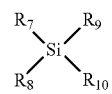

(IX)

wherein, $R_9$ is chosen from halogen atoms and OR'$_9$ groups;

$R_{10}$ is chosen from halogen atoms and OR'$_{10}$ groups;

R'$_9$ and R'$_{10}$, which may be identical or different, are chosen from hydrogen, and linear and branched, saturated and unsaturated $C_1$-$C_{14}$ hydrocarbon groups;

$R_7$ is a non hydrolyzable functional group providing a cosmetic effect; and $R_8$ is a non hydrolyzable functional group bearing at least one function chosen from amines; and provided that at least one of $R_9$ and $R_{10}$ is not a halogen;

As used herein, the term "functional group providing a cosmetic effect" means a group derived from an entity chosen from reducing agents, oxidizing agents, coloring agents, polymers, surfactants, antibacterial agents, and UV absorbing filters.

In some instances, the at least one alkoxysilane comprising at least one solubilizing functional group may be chosen from compounds of formula (XI):

$$(R_{21}O)_x(R_{22})_y\text{Si-}(A)_p\text{-}[NR_{23}\text{-}(A')_{p'}]_q\text{-}[NR'_{23}\text{-}(A'')_{p''}]$$
$$_y\text{Si—}(R'_{22})_{y'}(OR'_{21})_{x'} \qquad (XI)$$

wherein, $R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x is an integer ranging from 1 to 3;

y is 3−x;

x' is an integer ranging from 1 to 3;

y' is 3−x', p, p', p'', q, and q' can each be 0 or 1, wherein at least one of q or q' is not equal to zero;

A, A', and A'', which may be identical or different, are chosen from linear and branched $C_1$-$C_{20}$ alkylene divalent radicals; and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The alkoxysilane comprising at least one solubilizing functional group may also be chosen from compounds of formula (XII):

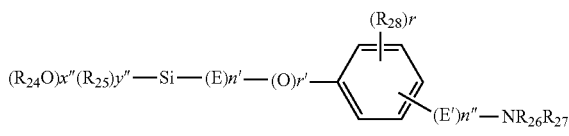
(XII)

wherein, $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x'' is 2 or 3;

y'' is 3−x'';

n' is 0 or 1;

n'' is 0 or 1;

E and E', which may be identical or different, are chosen from linear and branched $C_1$-$C_{20}$ alkylene divalent radicals;

$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;

r is an integer ranging from 0 to 4;

r'=0 or 1; and $R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

In some cases, the at least one alkoxysilane comprising at least one solubilizing functional group may be chosen from compounds of formula (XIII):

$$(R_{29}O)x_1(R_{30})y_1\text{-Si-}(A_1)_s\text{-CH}=O \qquad (XIII)$$

wherein, $R_{20}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

$x_1$ is 2 or 3;

$y_1$ is 3−$x_1$;

$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups; and s is 0 or 1.

Furthermore, in some cases, the at least one alkoxysilane comprising at least one solubilizing functional group is chosen from compounds of formula (XIV):

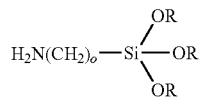

wherein the R radicals, which may be identical or different, are chosen from $C_1$-$C_6$ alkyl radicals and n is an integer ranging from 1 to 6, for example, from 2 to 4.

Alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein.

Other useful alkoxysilanes are alkoxysilanes comprising at least one hydrocarbon chain containing amino functions. In this respect, non-limiting mention may be made of the N-[(3-trimethoxysilyl)propyl]ethylenediamine and N,N'-Bis[(3-trimethoxysilyl)propyl]ethylenediamine compounds supplied by GELEST.

Non-limiting examples of useful alkoxysilanes include aminoalkyltrialkoxysilanes such as 3-aminopropyltriethoxysilane ("APTES", described in French Patent Application No. FR 2 789 896, incorporated herein by reference), and mixtures thereof.

Exemplary cationic silanes that may be used according to various embodiments of the disclosure include, but are not limited to, organosilanes and derivatives thereof, such as alkylsilanes, allylsilanes, and alkoxysilanes.

In some cases, the cationic silane may be chosen from alkoxysilanes comprising at least one solubilizing functional group, such as for example, methoxysilanes, triethoxysilanes, aminopropyltriethoxysilane, methyltriethoxysilane, and derivatives thereof and mixtures thereof. As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In some cases, the alkoxysilane comprising at least one solubilizing functional group may comprise two or three alkoxy functions. Likewise, in some cases, the alkoxy functional groups are chosen from methoxy and ethoxy functional groups.

According to some embodiments, the alkoxysilane comprising at least one solubilizing functional group present in the composition of the present disclosure is chosen from compounds of formula (VIII):

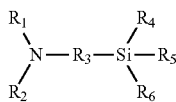
(VIII)

wherein,
$R_4$ is chosen from halogen atoms, OR' groups, and $R_{11}$ groups;
$R_5$ is chosen from halogen atoms, OR'' groups, and $R_{12}$ groups;
$R_6$ is chosen from halogen atoms, OR''' groups, and $R_{13}$ groups;
$R_1$, $R_2$, $R_3$, R'. R'', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R'', and R''' may also be chosen from hydrogen;
provided that at least two groups $R_4$, $R_5$, and $R_6$ are different from $R_{11}$, $R_{12}$, and $R_{13}$, and at least two groups R', R'', and R''' are not hydrogen.

The alkoxysilane comprising at least one solubilizing functional group may also be chosen from compounds of formula (IX):

(IX)

wherein,
$R_9$ is chosen from halogen atoms and OR'$_9$ groups;
$R_{10}$ is chosen from halogen atoms and OR'$_{10}$ groups;
R'$_9$ and R'$_{10}$, which may be identical or different, are chosen from hydrogen, and linear and branched, saturated and unsaturated $C_1$-$C_{14}$ hydrocarbon groups;
$R_7$ is a non hydrolyzable functional group providing a cosmetic effect; and
$R_6$ is a non hydrolyzable functional group bearing at least one function chosen from amines; and
provided that at least one of $R_9$ and $R_{10}$ is not a halogen;
As used herein, the term "functional group providing a cosmetic effect" means a group derived from an entity chosen from reducing agents, oxidizing agents, coloring agents, polymers, surfactants, antibacterial agents, and UV absorbing filters.

In some instances, the at least one alkoxysilane comprising at least one solubilizing functional group may be chosen from compounds of formula (XI):

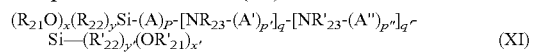
(XI)

wherein,
$R_{21}$, $R_{22}$, R'$_{21}$, and R'$_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;
x is an integer ranging from 1 to 3;
y is 3−x;
x' is an integer ranging from 1 to 3;
y' is 3−x'',
p, p', p'', q, and q' can each be 0 or 1, wherein at least one of q or q' is not equal to zero;
A, A', and A'', which may be identical or different, are chosen from linear and branched $C_1$-$C_{20}$ alkylene divalent radicals; and
$R_{23}$ and R'$_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The alkoxysilane comprising at least one solubilizing functional group may also be chosen from compounds of formula (XII):

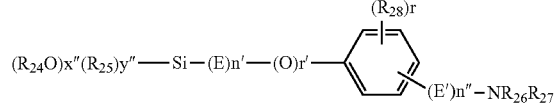
(XII)

wherein,

R$_{24}$ and R$_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x" is 2 or 3;

y" is 3−x";

n' is 0 or 1;

n" is 0 or 1;

E and E', which may be identical or different, are chosen from linear and branched C$_1$-C$_{20}$ alkylene divalent radicals;

R$_{26}$ and R$_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, C$_1$-C$_{20}$ alcohol ester, amine, carboxyl, alkoxysilane, C$_6$-C$_{30}$ aryl, hydroxyl, and carbonyl groups, and aromatic, heterocyclic, and non-heterocyclic rings, optionally substituted with at least one group chosen from C$_1$-C$_{20}$ alcohol ester, amine, amide, carboxyl, alkoxysilane, hydroxyl, carbonyl, and acyl groups;

r is an integer ranging from 0 to 4;

r'=0 or 1; and

R$_{25}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

In some cases, the at least one alkoxysilane comprising at least one solubilizing functional group may be chosen from compounds of formula (XIII):

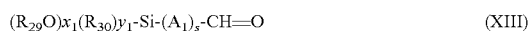
(R$_{29}$O)$x_1$(R$_{30}$)$y_1$-Si-(A$_1$)$_s$-CH=O    (XIII)

wherein,

R$_{29}$ and R$_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x$_1$ is 2 or 3;

y$_1$ is 3−x$_1$;

A$_1$ is chosen from linear and branched C$_1$-C$_{20}$ alkylene divalent radicals, optionally interrupted by or substituted with at least one group chosen from C$_1$-C$_{30}$ alcohol ester, amine, carboxyl, alkoxysilane, C$_6$-C$_{30}$ aryl, hydroxyl, and carbonyl groups; and s is 0 or 1, Furthermore, in some cases, the at least one alkoxysilane comprising at least one solubilizing functional group is chosen from compounds of formula (XIV):

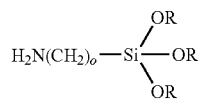

wherein the R radicals, which may be identical or different, are chosen from C$_1$-C$_6$ alkyl radicals and n is an integer ranging from 1 to 6, for example, from 2 to 4.

Alkoxysilanes useful in the present disclosure can be chosen from alkoxysilanes comprising a silicon atom in a formula R$_{(4-n)}$SiX$_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein.

Other useful alkoxysilanes are alkoxysilanes comprising at least one hydrocarbon chain containing amino functions. In this respect, non-limiting mention may be made of the N-[(3-trimethoxysilyl)propyl]ethylenediamine and N,N'-Bis [(3-trimethoxysilyl)propyl]ethylenediamine compounds supplied by GELEST. Further, non-limiting examples of useful alkoxysilanes include aminoalkyltrialkoxy silanes such as 3-aminopropyltriethoxysilane, and mixtures thereof.

The cationic silane layer of (a), in some cases, is an aminoalkoxysilane layer, for example, a compound of the following formula:

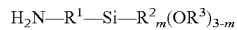
H$_2$N—R$^1$—Si—R$^2_m$(OR$^3$)$_{3-m}$ wherein

R$^1$ is C$_1$-C$_6$-alkylene, C$_5$-C$_6$-cycloalkylene or C$_5$-C$_6$-arylene, each of which may be optionally substituted by one or two C$_1$-C$_3$-alkyl groups, and R$^2$ and R$^3$, independently of one another, are C$_1$-C$_6$-alkyl or C$_5$-C$_6$-cycloalkyl, each of which may optionally be substituted by one or two C$_1$-C$_3$-alkyl groups, and m is 0, 1 or 2.

In some instances, the aminoalkoxysilane may be selected from the group consisting of 3-aminopropyltrimethoxysilane, N-(2-aminoethyl)-3-aminopropyltrimethoxysilane, (3-triethoxysilylpropyl)-diethylenetriamine, 3-aminopropyltriethoxysilane (APTES), N-(2-aminoethyl)-3-amino-propyltriethoxysilane, (3-triethoxysilylpropyl)-diethylentriamine, 3-aminoethyltriethoxysilane (AETES), 3-aminopropylmethyldiethoxysilane (APMDES), and N-cyclohexylaminomethyltriethoxysilane. Likewise, in some cases, the aminoalkoxysilane is aminoalkoxysilane is 3-aminopropyltriethyoxysilane (APTES).

Anionic Polymers

Anionic polymers may be polymers with anionic groups distributed along the polymer backbone. Anionic groups, which may include carboxylate, sulfonate, sulphate, phosphate, nitrate, or other negatively charged or ionizable groupings, may be disposed upon groups pendant from the backbone or may be incorporated in the backbone itself.

Anionic polymers useful herein include, for example: Polyacrylic acid; Polymethacrylic acid; Carboxyvinylpolymer; acrylate copolymers such as Acrylate/C 10-30 alkyl acrylate crosspolymer, Acrylic acid/vinyl ester copolymer/AcrylatesNinyl Isodecanoate crosspolymer, Acrylates/Palmeth-25 Acrylate copolymer, Acrylate/Steareth-20 Itaconate copolymer, and Acrylate/Celeth-20 Itaconate copolymer; sulfonate polymers such as Polysulfonic acid, Sodium Polystyrene Sulfonate supplied from Akzo Nobel under the tradename FLEXAN II, copolymers of methacrylic acid and acrylamidomethylpropane sulfonic acid, and copolymers of acrylic acid and acrylamidomethylpropane sulfonic acid;

carboxymethycellulose; carboxy guar gum; copolymers of ethylene and maleic acid; and acrylate silicone polymer. In some instances, the anionic polymers include, for example, Carbomer supplied from Noveon under the tradename Carbopol® 981 and Carbopol® 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic; acrylates copolymer having the tradename CARBOPOL® Aqua SF-1 and available from Lubrizol as an aqueous dispersion, and acrylates crosspolymer-4 having the tradename CARBOPOL® Aqua SF-2 and available from Lubrizol as an aqueous dispersion.

Cationic Polymers

The expression "cationic polymer" denotes any polymer containing cationic groups or groups which can be ionized into cationic groups. The cationic polymers may be those that contain units containing primary, secondary, tertiary and/or quaternary amine groups which can either form part of the main polymer chain or which can be borne by a side substituent that is directly attached thereto. The cationic polymers used generally have a molecular mass of between 500 and $5 \times 10^6$ approximately and preferably between $10^3$ and $3 \times 10^6$ approximately.

Among the cationic polymers, mention may be made more particularly of a polyacrylamide having quaternary ammonium groups. A suitable example of a polyacrylamide having quaternary ammonium groups is polyacrylamidopropyltrimonium chloride (INCI name), a highly charged polymer, also described as a homopolymer of acrylamido-N-propyltrimethylammonium chloride and commercially available from the company Ashland under the tradename N-DurHance™ A-1000.

Among the cationic polymers, mention may be made more particularly of quaternized proteins (or protein hydrolysates) and polymers of the polyamine, polyaminoamide and quaternary polyammonium type. These are known products.

The quaternized proteins or protein hydrolysates are, in particular, chemically modified polypeptides bearing quaternary ammonium groups at the end of the chain or grafted thereto. Their molecular mass can range, for example, from 1500 to 10,000 and in particular from 2000 to 5000 approximately. Among these compounds, mention may be made in particular of:

collagen hydrolysates bearing triethyl-ammonium groups, such as the products sold under the name "Quat-Pro E" by the company Maybrook and referred to in the CTFA dictionary as "Triethonium Hydrolyzed Collagen Ethosulfate";

collagen hydrolysates bearing trimethyl-ammonium and trimethylstearylammonium chloride groups, sold under the name "Quat-Pro S" by the company Maybrook and referred to in the CTFA dictionary as "Steartrimonium Hydrolyzed Collagen";

protein hydrolysates bearing, on the polypeptide chain, quaternary ammonium groups containing at least one alkyl radical having from 1 to 18 carbon atoms. Among these protein hydrolysates, mention may be made; inter alia, of:

"Croquat L" in which the quaternary ammonium groups contain a $C_{12}$ alkyl group; "Croquat M" in which the quaternary ammonium groups contain $C_{10}$-$C_{18}$ alkyl groups; "Croquat S" in which the quaternary ammonium groups contain a $C_{18}$ alkyl group; "Crotein Q" in which the quaternary ammonium groups contain at least one alkyl group having 1 to 18 carbon atoms. These various products are sold by the company Croda. Other quaternized proteins or hydrolysates are, for example, those corresponding to the formula:

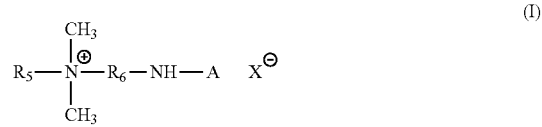

(I)

in which $X^{\ominus}$ is an anion of an organic or inorganic acid, A denotes a protein residue derived from collagen protein hydrolysates, $R_5$ denotes a lipophilic group containing up to 30 carbon atoms and $R_6$ represents an alkylene group having 1 to 6 carbon atoms. Mention may be made, for example, of the products sold by the company Inolex under the name "Lexein OX 3000", referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the name "Hydrotriticum WO or QM", referred to in the CTFA dictionary as "Cocodimonium Hydrolysed Wheat Protein", "Hydrotriticum QL", referred to in the CTFA dictionary as "Lauridimonium Hydrolysed Wheat Protein" or alternatively "Hydrotriticum QS", referred to in the CTFA dictionary as "Steardimonium Hydrolysed Wheat Protein". Cationic proteins can also be non-quaternized proteins that have an inherent cationic charge by having a preponderant basic amino acids Another family of cationic polymers is that of cationic silicone polymers. Among these polymers, mention may be made of:

(a) silicone polymers corresponding to formula (II) below:

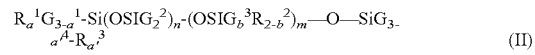

(II)

in which:

$G^1$, $G^2$, $G^3$ and $G^4$, which may be identical or different, denote a hydrogen atom, a phenyl group, an OH group, a $C_1$-$C_{18}$ alkyl group, for example methyl, a $C_2$-$C_{13}$ alkenyl group or a $C_1$-$C_{18}$ alkoxy group, a and a', which may be identical or different, denote the number 0 or an integer from 1 to 3, in particular 0, b denotes 0 or 1 and in particular 1, m and n are numbers such that the sum (n+m) can range especially from 1 to 2000 and in particular from 50 to 150, it being possible for n to denote a number from 0 to 1999 and in particular from 49 to 149 and it being possible for m to denote a number from 1 to 2000 and in particular from 1 to 10, $R_1$, $R_2$, $R_3$ and $R_4$, which may be identical or different, denote a monovalent radical of formula —$C_qH_{2q}O_sR^5_tL$ in which q is a number from 1 to 8, s and t, which may be identical or different, are equal to 0 or 1, $R^5$ denotes an optionally hydroxylated alkylene group and L is an optionally quaternized amine group chosen from the groups:

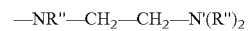

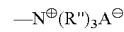

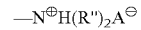

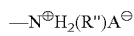

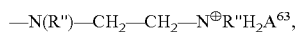

in which R″ can denote hydrogen, phenyl, benzyl or a monovalent saturated hydrocarbon-based radical, for example an alkyl radical having from 1 to 20 carbon atoms and $A^{\ominus}$ represents a halide ion such as, for example, fluoride, chloride, bromide or iodide. Products corresponding to this definition are, for example, the polysiloxanes referred to in the CTFA dictionary as "Amodimethicone" and corresponding to formula (II) below:

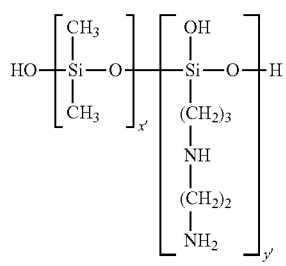

in which x' and y' are integers dependent on the molecular weight, generally such that the said molecular weight is between 5000 and 20,000 approximately.

A product corresponding to formula (II) is the polymer referred to in the CTFA dictionary as "Trimethylsilylamodimethicone", corresponding to the formula:

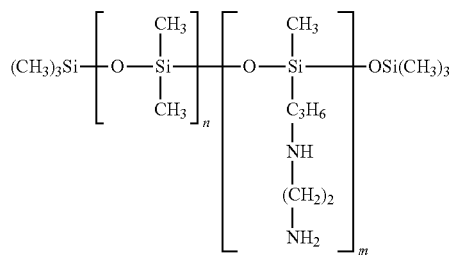

in which n and m have the meanings given above (cf. formula II),

A commercial product corresponding to this definition is a mixture (90/10 by eight) of a poly-dimethylsiloxane containing aminoethyl aminoisobutyl groups and of a polydimethylsiloxane, sold under the name "Q2-8220" by the company Dow Corning. Such polymers are described, for example, in patent application EP-A-95238.

Other polymers corresponding to formula (II) are the silicone-based polymers corresponding to the following formula:

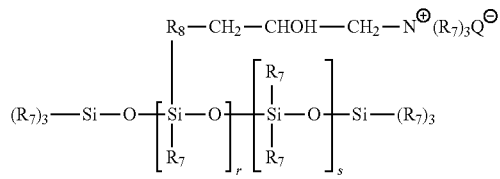

in which:

$R_7$ represents a monovalent hydrocarbon-based radical having from 1 to 18 carbon atoms, and in particular a $C_{1-C18}$ alkyl or $C_2-C_{18}$ alkenyl radical, for example methyl;

$R_8$ represents a divalent hydrocarbon-based radical, in articular a $C_{1-C18}$ alkylene radical or a $C_1-C_{18}$, for example $C_1-C_8$, divalent alkylenoxy radical;

$Q^{\ominus}$ is a halide ion, in particular chloride;

r represents an average statistical value from 2 to 20 and in particular from 2 to 8;

s represents an average statistical value from 20 to 200 and in particular from 20 to 50. Such polymers are described more particularly in U.S. Pat. No. 4,185,087. A polymer entering into this category is the polymer sold by the company Union Carbide under the name "Ucar Silicone ALE 563".

The polymers of the polyamine, polyaminoamide or polyquaternary ammonium type which can be used in accordance with the present invention and which can be mentioned in particular are those described in French patents Nos. 2,505,348 and 2,542,997. Among these polymers, mention may be made of:

(1) Quaternized or non-quaternized vinyl-pyrrolidone/dialkylaminoalkyl acrylate or methacrylate copolymers, such as the products sold under the name "Gafquat" by the company ISP, such as, for example, "Gafquat 734, Gafquat 755 or Gafquat HS100" or alternatively the products known as "Copolymer 937" or "Copolymer 845". These polymers are described in detail in French patents 2,077,143 and 2,393,573.

(2) The cellulose ether derivatives containing quaternary ammonium groups described in French patent 1,492,597, and in particular the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyl-diallylammonium salt. The commercial products corresponding to this definition are, more particularly, the products sold under the names "Celquat L 200" and "Celquat H 100" by the company National Starch.

(4) Cationic polysaccharides, and in particular guar gums, described more particularly in U.S. Pat. Nos. 3,589,578 and 4,031,307 and more particularly the products sold under the names "Jaguar C 13 S", "Jaguar C 15" and "Jaguar C 17" sold by the company Meyhall.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2,162,025 and 2,280,361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide; these polyaminoamides can be alkylated or, if they contain one or more tertiary amine functions, they can be quaternized. Such polymers are described in particular in French patents 2,252,840 and 2,368,508.

(7) Polyaminoamide derivatives resulting from the condensation of polyalkylenepolyamines with polycarboxylic adds followed by an alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1,583,363. Among these derivatives, mention may be made more particularly of the adipic acid/dimethylamino-polymers sold under the name "Cartaretine F", "Cartaretine F4" or "Cartaretine F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms, the molar ratio between the polyalkylenepolyamine and the dicarboxylic acid being between 0.8:1 and 1.4:1, the polyaminoamide resulting therefrom being reacted with the epichlorohydrin in a molar ratio of epichlorohydrin relative to the secondary amine group in the polyaminoamide of between 0.5:1 and 1.8:1. Such polymers are described in particular in U.S. Pat. Nos. 3,227,615 and 2,961,347. Polymers of this type are sold in particular under the name "Hercosett 57" by the company Hercules Inc. or under the name "PD 170" or "Delsette 101" by the company Hercules in the case of the adipic acid/epoxypropyl/diethylenetriamine copolymer.

(9) Methyldiallylamine or dimethyldiallyl-ammonium cyclopolymers such as polymers containing, as constituents of the chain, units corresponding to formula (VI) or (VI'):

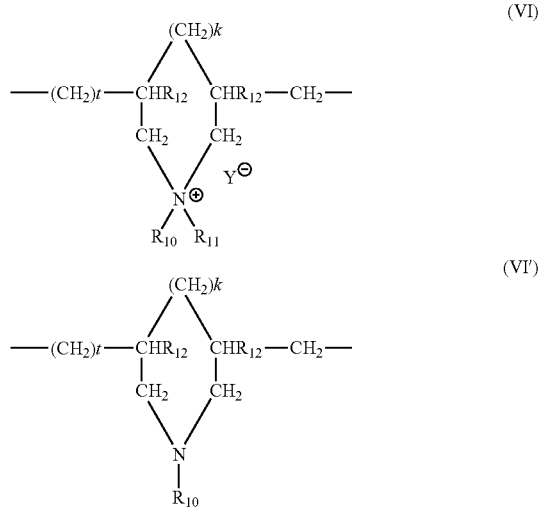

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, a lower amidoalkyl group or $R_{10}$ and $R_{11}$ can denote, together with the nitrogen atom to which they are attached, heterocyclic groups such as piperidyl or morpholinyl; $Y^{\ominus}$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallyl-ammonium chloride homopolymer sold under the name "Merguat 100" by the company Merck, and the copolymers of dimethyldiallylammonium chloride and of acrylamide sold under the name "Merquat 550".

(10) The quaternary diammonium polymer containing repeating units corresponding to the formula:

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group in which $R_{17}$ is an alkylene and D is a quaternary ammonium group;

$A_1$ and $B_1$ represent polymethylene groups containing from 2 to 20 carbon atoms which can be linear or branched, saturated or unsaturated, and which can contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^{\ominus}$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical $B_1$ can also denote a group $(CH_2)_n$—CO-D-OC—$(CH_2)_n$ in which D denotes:

a) a glycol residue of formula: —O—Z—O, in which Z denotes a linear or branched hydrocarbon radical or a group corresponding to one of the following formulae:

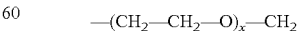
—$(CH_2$—$CH_2$—$O)_x$—$CH_2$

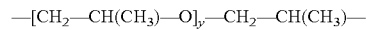
—$[CH_2$—$CH(CH_3)$—$O]_y$—$CH_2$—$CH(CH_3)$— in which x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH, in which Y denotes a linear or branched hydrocarbon-based radical or alternatively the divalent radical

—CH$_2$—CH$_2$—S—S—CH$_2$—CH$_2$—;

d) a ureylene group of formula:

NH—CO—NH—.

In some cases, X$^\ominus$ is an anion such as chloride or bromide.

These polymers have a molecular mass generally of between 1000 and 100,000. Polymers of this type are described in articular in French patents 2,320,330, 2,270, 846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Polyquaternary ammonium polymers consisting of units of formula (VIII):

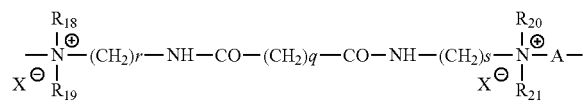

in which formula:

R$_{18}$, R$_{19}$, R$_{20}$ and R$_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$ OH radical, in which p is equal to 0 or to an integer between 1 and 6, with the proviso that R$_{18}$, R$_{19}$, R$_{20}$ and R$_{21}$ do not simultaneously represent a hydrogen atom, r and s, which may be identical or different, are integers between 1 and 6, q is equal to 0 or to an integer between 1 and 34, X denotes a halogen atom, A denotes a radical of a dihalide or preferably represents —CH$_2$—CH$_2$—O—CH$_2$—CH$_2$—. Such compounds are described in particular in patent application EP-A-122,324. Among those, mention may be made, for example, of the products "Mirapol A 15", "Mirapol 10 AD1", "Mirapol AZ1" and "Mirapol 175" sold by the company Miranol.

(12) Homopolymers or copolymers derived from acrylic or methacrylic acid and containing units:

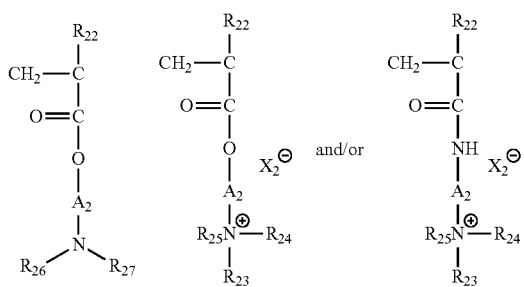

in which the groups R$_{22}$ independently denote H or CH$_3$, the groups A$_2$ independently denote a linear or branched alkyl group of 1 to 6 carbon atoms or a hydroxyalkyl group of 1 to 4 carbon atoms, the groups R$_{23}$, R$_{24}$ and R$_{25}$, which may be identical or different, independently denote an alkyl group of 1 to 18 carbon atoms or a benzyl radical, the groups R$_{26}$ and R$_{27}$ represent a hydrogen atom or an alkyl group of 1 to 6 carbon atoms, X$_2^\ominus$ denotes an anion, for example methosulphate or halide, such as chloride or bromide.

The comonomer(s) which can be used in the preparation of the corresponding copolymers belong(s) to the family of acrylamides, methacrylamides, diacetone acrylamides, acrylamides and methacrylamides substituted on the nitrogen with lower alkyls, alkyl esters, acrylic or methacrylic adds, vinylpyrrolidone or vinyl esters.

(13) Quaternary vinylpyrrolidone and vinyl-imidazole polymers such as, for example, the products sold under the names "Luviquat FC 905", "Luviquat FC 550" and "Luviquat FC 370" by the company BASF.

(14) Polyamines such as "Polyquart H" sold by Henkel referred to under the name "Polyethylene glycol (15) Tallow Polyamine" in the CTFA dictionary,

(15) Methacryloyloxyethyltrimethylammonium chloride crosslinked polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. An acrylamide/methacryloyloxyethyltrimethylammonium chloride crosslinked copolymer (20/80 by weight) in the form of a dispersion containing 50% by weight of the said copolymer in mineral oil can be used more particularly. This dispersion is sold under the name "Salcare SC 92" by the company Allied Colloids. A methacryloyloxyethyltrimethylammonium chloride crosslinked homopolymer containing about 50% by weight of the homopolymer in mineral oil can also be used. This dispersion is sold under the name "Salcare SC 95" by the company Allied Colloids.

Other cationic polymers which can be used in the context of the disclosure are polyalkyleneimines, in particular polyethyleneimines, polymers containing vinylpyridine or vinylpyridinium units, condensates of polyamines and of epichlorohydrin, quaternary polyureylenes and chitin derivatives.

Among all of the cationic polymers which can be used in the context of the present disclosure, mention is made of a polyacrylamide having quaternary ammonium groups such Polyacrylamidopropyltrimonium Chloride, sold under the tradename N-DurHance™ A-1000 by the company Ashland, quaternized or non-quaternized vinylpyrrolidone/dialkylaminoalkyl acrylate or methacrylate copolymers, such as the products sold under the name "Gafquat" by the company ISP, such as, for example, "Gafquat 734, Gafquat 755 or Gafquat HS 100" or alternatively the products known as "Copolymer 937" or "Copolymer 845" also sold by the company ISP, and quaternary vinylpyrrolidone and vinylimidazole polymers such as the products sold under the names "Luviquat FC 905", "Luviquat FC 550" and "Luviquat FC 370" by the company BASF.

In some cases, the cationic polymer may be polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

The compositions comprising the cationic silanes, the anionic polymers, and the optional cationic polymers, may take various forms and consistencies, such that the compositions can be provided in the form of a solution, liquid emulsion, a liquid-lotion, liquid-gel, liquid-cream, such as a thick cream or gel-cream, or a foam or mousse.

Implementation of the present disclosure is provided by way of the following examples. The examples serve to illustrate the technology without being limiting in nature. For instance, the examples apply various component to hair to form layers by spraying a solution comprising the components on the hair, but application of the components to the hair is not limited to spraying (any application method can be used).

EXAMPLE

Example 1

Coloration Process

Regular bleached hair swatches were colored with Excellence Crème Nuance 6RR or Nutrisse 69, commercially available permanent red shade hair dye products that are known for their propensity to fade with washing. The colorant mixture (colorant+developer) was prepared according to the product instructions. The colorant and the developer were uniformly mixed immediately prior to application to the hair. The colorant mixture was applied to the hair and allowed to remain on the hair for 30 minutes. After 30 minutes, the hair swatches were rinsed thoroughly with tap water at 40° C. and 90 gallons per hour (GPH) flow rate until the water ran clear, then gently blotted with a towel to remove excess water. The rinse did not exceed 3 minutes. The hair swatches were then dried at room temperature overnight (at least 16 hours).

Example 2

Formation of a Layer-by-Layer (LbL) Film

After the colored hair swatches of Example 1 were dried, each side of the hair swatches were sprayed with a 10 wt. %, 12 wt. %, or 16 wt. % aqueous solution a cationic silane (3-aminopropyltriethoxysilane (APTES)), or with deionized water for a control. One side of the hair swatches was sprayed 10 times and then combed through 3 times to ensure even application. Then the other side of the hair swatches was sprayed 10 times with the same solution and the hair swatches were again combed through 3 times to ensure even application. Thus, a total of 20 sprays (2.8 g solution) per hair swatch were applied. The aqueous solution was left on the hair swatches for 20 minutes before the hair swatches were blown dry at low heat for 2 minutes.

After blow drying, each side of the hair swatches were sprayed with 1 wt. % aqueous solution of an anionic polymer (sodium polystyrene sulfonate (PSS)) or deionized water for a control. One side of the hair swatches was sprayed 10 times and then combed through 3 times to ensure even application. Then the other side of the hair swatches was sprayed 10 times with the same solution and the hair swatches were again combed through 3 times to ensure even application. Thus, a total of 20 sprays (2.8 g solution) per hair swatch were applied. The aqueous solution was left on the hair swatches for 5-10 minutes (without blow drying).

After application of the anionic polymer, each side of the hair swatches were sprayed with aqueous solutions of cationic polymer, Some swatches were treated with 1 wt. % of polyacrylamidopropyltrimonium chloride. Other swatches were treated with 10 wt. % or 12 wt. % 3-aminopropyltriethoxysilane (APTES). And finally, some swatches were treated with deionized water for a control. One side of the hair swatches was sprayed 10 times and then combed through 3 times to ensure even application. Then the other side of the hair swatches was sprayed 10 times with the same solution and the hair swatches were again combed through 3 times to ensure even application. Thus, a total of 20 sprays (2.8 g solution) per hair swatch were applied. The aqueous solution was left on the hair swatches for 20 minutes before the hair swatches were blown dry at low heat for 2 minutes.

The table below shows the weight percent ratios of the layers (weight percent ages are based on 100% active material).

| Treatment | Layer 1 wt % | Layer 2 wt % | Layer 3 wt % | Layers ratio |
|---|---|---|---|---|
| APTES/PSS/Poly-A* | 16 | 1 | 1 | 1:0.06:0.06 |
| APTES/PSS/APTES | 12 | 1 | 12 | 1:0.08:1 |
| APTES/PSS/APTES | 10 | 1 | 10 | 1:0.1:1 |

*Poly-A is polyacrylamidopropyltrimonium chloride (INCI name), commercially available from the company Ashland under the tradename N-DURHANCE™ A-1000

Example 3

Shampoo (Fading) Study

The LbL treated hair swatches and the control hair swatches from Example 2, and three commercially available hair color protection benchmarks were tested in duplicates or triplicates. The initial $L^*$, $a^*$, $b^*$ values of the swatches were taken.

The position on the ordinate (z-axis) representing brightness is designated by $L^*$, The hair swatches were shampooed with DOP shampoo (0.33 gram DOP/gram hair) for 4, 7, and 10 cycles. Each cycle entailed a 15 second shampoo followed by a 10 second rinse with tap water (40° C., 90 GPH). The swatches were blotted with a towel to remove excess water and then blow dried for 2 minutes with low heat. The day after treatment (24 hours), the Initial $L^*$, $a^*$, $b^*$ measurements were taken at 0 shampoos. Then the hair swatches were shampooed 4, 7, 10, 15, or 20 times and the $L^*$, $a^*$, $b^*$ measurements were again taken. The $\Delta E$ value is the difference in color of the hair swatch from its initial value before washing and final value after washing, based on $L^*a^*b^*$ parameters. $\Delta E$ of each hair swatch sample was taken in order to determine degree of color fading of treated hair swatches in comparison to controls. A lower $\Delta E$ represents less change in hair color (less color fading); therefore a lower $\Delta E$ is desirable.

The table below shows the average $\Delta E$ values of control hair swatches, the LbL treated hair swatches, and commercial benchmarks.

| | | Shampoos | | | | |
|---|---|---|---|---|---|---|
| Shade | Treatment | 4 | 7 | 10 ΔE | 15 | 20 |
| NT 69 | Untreated control for commercial formulas | 4.27 | 5.58 | 6.70 | | |
| NT 69 | Commerical formula 1 (for color-treated hair) | 3.97 | 5.05 | 6.99 | | |
| NT 69 | Commercial formula 2 (for color-treated hair) | 4.58 | 6.03 | 6.48 | | |
| NT69 | Untreated control for LBL | 4.40 | 5.15 | 6.13 | 6.96 | 7.37 |
| NT69 | 16% APTES/1% PSS/ 1% Poly-A | 1.92 | 2.70 | 4.00 | 4.54 | 6.05 |
| NT69 | 12% APTES/1% PSS/ 12% APTES | 2.67 | 2.60 | 2.77 | 4.03 | 4.66 |
| NT69 | 10% APTES/1% PSS/ 10% APTES | 2.76 | 3.63 | 4.47 | 5.52 | 5.74 |

The data shows that the LBL treated hair swatches had lower ΔE values than untreated hair (control). In the case of commercial benchmarks, again the LBL treated treated hair swatches had lower ΔE values. Thus, the data shows that the LBL films provide significant color protection (prevention of color fading).

The multilayer films may be referred to as a "polyelectric multilayer," which is a composition formed by sequential and repeated application of alternating anionic and cationic polymer layers, and optionally surface-treated with a cationic polymer layer. The term applies to a single cationic polymer layer coated with a single cationic polymer layer (that is optionally surface treated with a cationic polymer) and also to multiple alternating cationic polymer and anionic polymer layers, which are then optionally surface-treated with a cationic polymer.

As mentioned above, "LbL films" are films assembled by serial application of individual layers that associate with one another through non-covalent interactions. LbL films may be constructed to have any of a variety of film architectures, (e.g., number of layers, thickness of individual layers (understanding that "merging" of layer materials may occur once films are assembled), overall film thickness, etc.). In general, LbL films comprise multiple layers. In some cases, LbL films are comprised of multilayer units; each unit comprising individual layers. In accordance with the present disclosure, individual layers in an LbL film interact with one another. In particular, a layer in an LbL film comprises an interacting moiety, which interacts with that from an adjacent layer, so that a first layer associates with a second layer adjacent to the first layer, each contains at least one interacting moiety. In some cases, adjacent layers are associated with one another via non-covalent interactions. Exemplary non-covalent interactions include, but are not limited to, hydrogen bonding, affinity interactions, metal coordination, physical adsorption, host-guest interactions, hydrophobic interactions, pi stacking interactions, hydrogen bonding interactions, van der Waals interactions, magnetic interactions, dipole-dipole interactions and combinations thereof. In other cases, the the adjacent layer are associated by covalent bonding interactions. LbL films may be comprised of multilayer units with alternating layers of opposite charge, such as alternating anionic and cationic layers. For example, an electrostatic interaction can be a primary interaction; a hydrogen bonding interaction can be a secondary interaction between the two layers.

According to the present disclosure, LbL films may be comprised of one or more multilayer units. In some embodiments, an LbL film include a plurality of a single unit (e.g., a bilayer unit, a tetralayer unit, etc.). In some embodiments, an LbL film is a composite that include more than one units. For example, more than one unit can have different film materials (e.g., polymers), film architecture (e.g., bilayers, tetralayer, etc.), film thickness, and/or agents that are associated with one of the units. In some embodiments, an LbL film is a composite that include more than one bilayer units, more than one tetralayer units, or any combination thereof. In some embodiments, an LbL film is a composite that include a plurality of a single bilayer unit and a plurality of a single tetralayer unit. In some embodiments, the number of multilayer units is 3, 5, 10, 20, 30, 40, 50, 60, 70, 80, 90, 100, 150, 200, 300, 400 or even 500.

LbL films may have various thicknesses depending on methods of fabricating and applications. In some embodiments, an LbL film has an average thickness in a range of about 1 nm and about 100 μm. In some embodiments, an LbL film has an average thickness in a range of about 1 μm and about 50 μm. In some embodiments, an LBL film has an average thickness in a range of about 2 μm and about 5 μm. In some embodiments, the average thickness of an LBL film is or more than about 1 nm, about 5 nm, about 10 nm, about 20 nm, about 50 nm, about 75 nm, about 100 nm, about 200 nm, about 300 nm, about 400 nm, about 500 nm, about 600 nm, about 700 nm, about 800 nm, about 900 nm, about 1 .mu.m, about 1.5 .mu.m, about 2 .mu.m, about 3 .mu.m, about 4 .mu.m, about 5 .mu.m, about 10 .mu.m, about 20 .mu.m, about 50 .mu.m, about 100 .mu.m. In some embodiments, an LBL film has an average thickness in a range of any two values above.

The terms "comprising," "having," and "including" are used in their open, non-limiting sense.

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about" or recited without the term, regardless of whether the term "about" is specifically set forth (or is absent) in conjunction with any particular value.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for inhibiting color fading in artificially colored hair comprising:
    (a) applying a cationic aminoalkoxysilane layer on the artificially colored hair,
        wherein the aminoalkoxysilane is selected from the group consisting of 3-aminopropyltrimethoxysilane, N-(2-aminoethyl)-3-aminopropyltrimethoxysilane, (3-triethoxysilylpropyl)-diethylenetriamine, 3-aminopropyltriethoxysilane (APTES), N-(2-aminoethyl)-3-amino-propyltriethoxysilane, (3-triethoxysilylpropyl)-diethylentriamine, 3-aminoethyltriethoxysilane (AETES), 3-aminopropylmethyldiethoxysilane (APMDES), N-cyclohexylaminomethyltriethoxysilane, and a mixture thereof; and subsequently (b) applying an anionic polymer layer on the cationic aminoalkoxysilane layer, wherein the anionic polymer is selected from the group consisting of polyacrylic acid, polymethacrylic acid, carboxyvinylpolymer, an acrylate copolymer, a carboxymethycellulose a carboxy guar gum, a copolymer of ethylene and maleic acid, an acrylate silicone polymer, polysulfonic acid, a polystyrene sulfonate, a copolymer of methacrylic acid and acrylamidomethylpropane sulfonic acid, a copolymer of acrylic acid and acrylamidomethylpropane sulfonic acid, and a mixture thereof; and (c) optionally, repeating (a) and (b) to form additional layers;

thereby forming a layer-by-layer (LbL) film on the artificially colored hair.

2. The method of claim 1, further comprising:

(d) applying a cationic polymer surface layer to the LbL film, wherein the cationic polymer is a polyacrylamide having quaternary ammonium groups.

3. The method of claim 1, wherein the aminoalkoxysilane is 3-aminopropyltriethyoxysilane (APTES).

4. The method of claim 1, wherein the anionic polymer is a polystyrene sulphonate.

5. The method of claim 2, wherein the polyacrylamide having quaternary ammonium groups is a polyacrylamidopropyltrimonium.

6. The method of claim 1, wherein the LbL film is formed by:

(a) applying a solution comprising the cationic aminoalkoxysilane to the hair and forming the cationic aminoalkoxysilane layer; followed by (b) applying a separate solution comprising the anionic polymer to the cationic aminoalkoxysilane layer and forming the anionic polymer layer; and (c) optionally, repeating (a) and (b) to form additional layers.

7. The method of claim 6, further comprising:

(d) applying a solution comprising the cationic polymer to the LbL film and forming the cationic polymer surface layer wherein the cationic polymer is polyacrylamide having quaternary ammonium groups.

8. The method of claim 6, wherein the solutions comprising the cationic aminoalkoxysilane of (a), the anionic polymer of (b), and the cationic polymer of (d) are aqueous solutions.

9. A method for inhibiting color fading in artificially colored hair comprising:

(a) applying a solution comprising 0.1 wt. % to 25 wt. % of an aminoalkoxysilane to the artificially colored hair and forming a cationic polymer layer on the hair wherein the aminoalkoxysilane is selected from the group consisting of 3-aminopropyltrimethoxysilane, N-(2-aminoethyl)-3-aminopropyltrimethoxysilane, (3-triethoxysilylpropyl)-diethylenetriamine, 3-aminopropyltriethoxysilane (APTES), N-(2-aminoethyl)-3-amino-propyltriethoxysilane, (3-triethoxysilylpropyl)-diethylentriamine, 3-aminoethyltriethoxysilane (AETES), 3-aminopropylmethyldiethoxysilane (APMDES), N-cyclohexylaminomethyltriethoxysilane, and a mixture thereof; and subsequently (b) applying a solution comprising 0.1 wt. % to 5 wt. % of a polystyrene to the aminoalkoxysilane layer and forming an anionic polymer layer on the aminoalkoxysilane layer; and (c) optionally, repeating (a) and (b) to form one or more additional layers;

thereby forming a layer-by-layer (LbL) film on the artificially colored hair.

10. The method of claim 9, further comprising:

(d) applying a solution comprising 0.1 wt % to 20 wt. % of a polyacrylamide having quaternary ammonium groups to the LbL layer to form a cationic polymer surface layer.

* * * * *